United States Patent
Lygin et al.

(10) Patent No.: US 10,640,448 B2
(45) Date of Patent: May 5, 2020

(54) METHOD FOR PREPARING CARBOXYLIC ESTERS FROM ALDEHYDES

(71) Applicant: Evonik Operations GmbH, Essen (DE)

(72) Inventors: Alexander Lygin, Griesheim (DE); Steffen Krill, Muehltal (DE); Matthias Grömping, Darmstadt (DE); Andreas Tepperis, Bad Koenig (DE)

(73) Assignee: Evonik Operations GmbH, Essen (DE)

(*) Notice: Subject to any disclaimer, the term of this patent is extended or adjusted under 35 U.S.C. 154(b) by 0 days.

(21) Appl. No.: 15/967,463

(22) Filed: Apr. 30, 2018

(65) Prior Publication Data
US 2018/0334423 A1    Nov. 22, 2018

(30) Foreign Application Priority Data
May 17, 2017    (DE) ........................ 10 2017 208 313

(51) Int. Cl.
| | | |
|---|---|---|
| *C07C 67/44* | (2006.01) | |
| *B01J 31/02* | (2006.01) | |
| *B01J 21/04* | (2006.01) | |
| *B01J 21/06* | (2006.01) | |
| *B01J 23/04* | (2006.01) | |
| *B01J 23/10* | (2006.01) | |
| *B01J 23/14* | (2006.01) | |
| *B01J 23/18* | (2006.01) | |
| *B01J 23/34* | (2006.01) | |
| *B01J 23/72* | (2006.01) | |
| *C07C 69/54* | (2006.01) | |
| *B01J 21/08* | (2006.01) | |
| *B01J 21/12* | (2006.01) | |
| *B01J 21/14* | (2006.01) | |

(52) U.S. Cl.
CPC ............... *C07C 67/44* (2013.01); *B01J 21/04* (2013.01); *B01J 21/063* (2013.01); *B01J 21/066* (2013.01); *B01J 23/04* (2013.01); *B01J 23/10* (2013.01); *B01J 23/14* (2013.01); *B01J 23/18* (2013.01); *B01J 23/34* (2013.01); *B01J 23/72* (2013.01); *B01J 31/0212* (2013.01); *C07C 69/54* (2013.01); *B01J 21/08* (2013.01); *B01J 21/12* (2013.01); *B01J 21/14* (2013.01); *B01J 2531/31* (2013.01); *C07C 2531/14* (2013.01)

(58) Field of Classification Search
CPC ..... C07C 67/44; C07C 69/54; C07C 2531/14; B01J 21/063; B01J 21/066; B01J 21/08; B01J 23/04; B01J 23/10; B01J 23/14; B01J 23/18; B01J 23/34; B01J 23/72; B01J 2531/31; B01J 31/0212; B01J 21/12; B01J 21/14; B01J 21/04
See application file for complete search history.

(56) References Cited

U.S. PATENT DOCUMENTS

| | | | |
|---|---|---|---|
| 2,250,520 A | | 7/1941 | Bludworth |
| 2,516,627 A | * | 7/1950 | Hearne .................. C07C 67/44 560/210 |
| 2,998,447 A | | 8/1961 | Finch et al. |
| 5,070,066 A | | 12/1991 | Iijima |

FOREIGN PATENT DOCUMENTS

| | | | |
|---|---|---|---|
| JP | H05043514 A | | 7/1993 |
| WO | WO2003/049855 | * | 6/2003 |
| WO | WO/2003/049855 A1 | | 6/2003 |

OTHER PUBLICATIONS

WO2003/049855 Table 1 translation (Year: 2003).*
Ullmann's Encyclopedia of Industrial Chemistry, vol. 1, Acetaldehyde, pp. 191-207, 2012, Wiley-VCH Verlag GmbH & Co. KGaA, Weinheim.
Ullmann's Encyclopedia of Industrial Chemistry, vol. 1, Acrolein and Methacrolein, pp. 329-346, 2012, Wiley-VCH Verlag GmbH & Co. KGaA, Weinheim.

* cited by examiner

*Primary Examiner* — Jafar F Parsa
*Assistant Examiner* — Blaine G Doletski
(74) *Attorney, Agent, or Firm* — Grüneberg and Myers PLLC

(57) ABSTRACT

A method can prepare a carboxylic ester. The method includes reacting an aldehyde in the presence of an aluminium alkoxide applied to a support material.

7 Claims, No Drawings

METHOD FOR PREPARING CARBOXYLIC ESTERS FROM ALDEHYDES

This application claims priority to German Patent Application No. 10 2017 208 313.1, filed on May 17, 2017.

The invention relates to a method for preparing carboxylic esters from aldehydes using a heterogeneous catalyst and a method for preparing the catalyst.

Carboxylic esters are typically prepared by the acid-catalyzed reaction of alcohols with carboxylic acids (esterification) or by reaction of alcohols with other carboxylic esters (transesterification). In the case that certain alcohols are not readily accessible or are expensive, which applies to methallyl alcohol for example, it is more favourable to start from other more accessible raw materials, for example aldehydes. Furthermore, it is particularly advantageous if only one reactant rather than two has to be used for preparing the carboxylic esters.

These advantages are realized by the catalytic conversion of aldehydes to carboxylic esters. This reaction is also known in the prior art as the Tishchenko reaction or Claisen-Tishchenko reaction.

In this context, two aldehydes react by rearrangement in the presence of an aluminium alkoxide to give a carboxylic ester, corresponding to the following reaction scheme (here, for example, with aluminium triethoxide as catalyst):

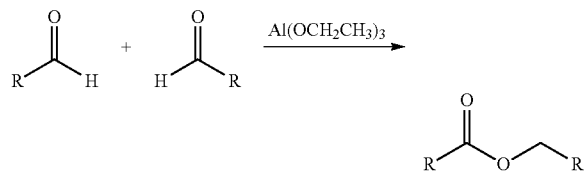

U.S. Pat. No. 2,516,627 describes the preparation of allyl acrylate by reacting acrolein in the presence of aluminium triisopropoxide (Al(OiPr)$_3$) in benzene as solvent. Al(OiPr)$_3$ is present in this case as a soluble homogeneous catalyst. Al(OiPr)$_3$ is prepared separately by reacting aluminium with isopropanol using a catalyst, such as mercuric chloride for example. The maximum yield of allyl acrylate in this method is 40%, and considerable amounts of allyl alcohol are isolated as by-product.

U.S. Pat. No. 2,250,520 describes the preparation of methallyl methacrylate from methacrolein in the presence of aluminium trimethallylalkoxide (Al(OMethallyl)$_3$) in benzene as solvent. The aluminium alkoxide is again present as a homogeneous catalyst. The catalyst is prepared in a separate reaction of aluminium with methallyl alcohol using mercuric chloride and iodine.

JP 05043514 A describes the preparation of methallyl methacrylate from methacrolein in the presence of an aluminium alkoxide, for example aluminium tri-n-butoxide. In this case, however, mixed esters are formed as by-products, i.e. carboxylic esters with n-butyl radicals, which can only be separated with difficulty from the methallyl methacrylate.

A fundamental problem in the methods described in the prior art is the use of a homogeneous catalyst which cannot be readily separated from the reaction products. U.S. Pat. No. 2,998,447 describes in this context the preparation of methallyl methacrylate from methacrolein in the presence of aluminium tri-sec-butoxide and the removal of the aluminium alkoxide from the reaction medium by distillation. However, this process requires a complex vacuum distillation in order to maintain a low thermal stress on the reaction medium.

The restriction to a homogeneous catalyst generally also has the consequence that the reaction of the aldehyde to the carboxylic ester has to be regularly interrupted in order to separate the catalyst from the reaction product and can therefore only be carried out discontinuously.

Against this background, it is an object of the present invention to provide a method for preparing carboxylic esters from aldehydes which results in good yields of carboxylic esters and enables easy removal of the catalyst without reducing activity of the catalyst. In addition, the method should allow reuse of the catalyst. Furthermore, a continuous process regime should be enabled.

This object is achieved by a method for preparing a carboxylic ester by reacting an aldehyde in the presence of an aluminium alkoxide applied to a support material.

The aluminium alkoxide to be used in accordance with the invention is applied to a support and as a result is present in the reaction medium as a heterogeneous catalyst. This significantly facilitates the removal of the catalyst since a distillative process is no longer required for the separation, but rather the catalyst can be removed by filtration under mild conditions. The catalyst thus isolated also maintains its activity and can be reused for further reactions. The use of a heterogeneous catalyst also enables a continuous process regime in which the catalyst, in the form of a fixed bed for example, is continuously traversed by the reaction medium, without the reaction having to be interrupted in order to separate the catalyst from the reaction product.

It has also been established that sufficiently high yields of carboxylic esters can be achieved by using supported aluminium alkoxides. In some cases, the yield achieved with the method according to the invention even significantly exceeds the yield achieved using a homogeneous catalyst.

The method according to the invention is particularly suitable for reacting aldehydes of the general formula (I):

$$R^1-CHO \qquad (I),$$

where $R^1$ is a —($C_1$-$C_{12}$)-alkyl group or a —($C_2$-$C_{12}$)-alkenyl group and $R^1$ may optionally be substituted by one or more substituents selected from —($C_1$-$C_{12}$)-alkyl, —($C_3$-$C_{12}$)-cycloalkyl, —($C_4$-$C_{12}$)-heterocycloalkyl, —($C_8$-$C_{20}$)-aryl, —($C_4$-$C_{20}$)-heteroaryl, —O—($C_1$-$C_{12}$)-alkyl, —O—($C_3$-$C_{12}$)-cycloalkyl, —S—($C_1$-$C_{12}$)-alkyl, —S—($C_3$-$C_{12}$)-cycloalkyl, —COO—($C_1$-$C_{12}$)-alkyl, —COO—($C_3$-$C_{12}$)-cycloalkyl, —CONH—($C_1$-$C_{12}$)-alkyl, —CONH—($C_3$-$C_{12}$)-cycloalkyl, —N—[($C_1$-$C_{12}$)-alkyl]$_2$, —OH, —NH$_2$, halogen.

Particularly preferred substituents are —($C_1$-$C_{12}$)-alkyl, —($C_2$-$C_{12}$)-alkenyl, —($C_3$-$C_{12}$)-cycloalkyl, —($C_6$-$C_{20}$)-aryl. Very particular preference is given to —($C_2$-$C_4$)-alkenyl substituents, particularly suitable in this case being the method according to the invention for reacting acrolein and/or methacrolein.

In the context of the invention, the following definitions of terms apply.

($C_1$-$C_{12}$)-alkyl groups are linear or branched alkyl groups having 1 to 12 carbon atoms. Suitable ($C_1$-$C_{12}$)-alkyl groups are especially methyl, ethyl, propyl, isopropyl, n-butyl, isobutyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1,1,2- trimethylpropyl, 1,2,2-trimethylpropyl, 1-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, nonyl, decyl.

($C_2$-$C_{12}$)-alkenyl groups are linear or branched alkenyl groups having 2 to 12 carbon atoms and one or more C—C double bonds. Suitable ($C_2$-$C_{12}$)-alkenyl groups are especially vinyl (ethenyl), allyl (propenyl) and methallyl (isobutenyl).

($C_3$-$C_{12}$)-cycloalkyl groups are cycloalkyl groups having 3 to 12 carbon atoms. Suitable ($C_3$-$C_{12}$)-cycloalkyl groups are especially cyclopropyl, cyclobutyl, cyclopentyl, cyclohexyl, cycloheptyl, cyclooctyl, cyclododecyl, cydopentadecyl, norbornyl, adamantyl.

($C_4$-$C_{12}$)-heterocycloalkyl groups are cycloalkyl groups having 4 to 12 carbon atoms and any number of heteroatoms. Preferred heteroatoms are O, N and S. Suitable ($C_4$-$C_{12}$)-heterocycloalkyl groups are especially tetrahydrothiophenyl, tetrahydrofuryl, tetrahydropyranyl and dioxanyl.

($C_8$-$C_{20}$)-aryl groups are aromatic hydrocarbon groups having 6 to 20 carbon atoms. Suitable ($C_8$-$C_{20}$)-aryl groups are especially phenyl, naphthyl, indenyl, fluorenyl, anthracenyl, phenanthrenyl, naphthacenyl, chrysenyl, pyrenyl, coronenyl. Preferred ($C_8$-$C_{20}$)-aryl groups are phenyl, naphthyl and anthracenyl.

($C_4$-$C_{20}$)-heteroaryl groups are aromatic hydrocarbon groups having 4 to 20 carbon atoms and any number of heteroatoms. Preferred heteroatoms are O, N and S. Suitable ($C_4$-$C_{20}$)-heteroaryl groups are especially furyl, thienyl, pyrrolyl, oxazolyl, isoxazolyl, thiazolyl, isothiazolyl, imidazolyl, pyrazolyl, furazanyl, tetrazolyl, pyridyl, pyridazinyl, pyrimidyl, pyrazinyl, benzofuranyl, indolyl, isoindolyl, benzimidazolyl, quinolyl, isoquinolyl.

Preferred halogen substituents are F, Cl and Br.

The group $R^1$ is preferably a —($C_2$-$C_{12}$)-alkenyl group which is optionally substituted as described above. $R^1$ is particularly preferably an unsubstituted —($C_2$-$C_{12}$)-alkenyl group. $R^1$ is most preferably vinyl, allyl or methallyl.

In one embodiment, the aldehyde is acrolein or methacrolein.

The aluminium alkoxide used is preferably a compound of the general formula (II):

$$Al(OR^2)_3 \quad\quad (II),$$

where each $R^2$ radical is independently of one another a —($C_1$-$C_{12}$)-alkyl group or a —($C_2$-$C_{12}$)-alkenyl group and each $R^2$ radical may independently of one another optionally be substituted by one or more substituents selected from —($C_1$-$C_{12}$)-alkyl, —($C_3$-$C_{12}$)-cycloalkyl, —($C_4$-$C_{12}$)-heterocycloalkyl, —($C_6$-$C_{20}$)-aryl, —($C_4$-$C_{20}$)-heteroaryl, —O—($C_1$-$C_{12}$)-alkyl, —O—($C_3$-$C_{12}$)-cycloalkyl, —S—($C_1$-$C_{12}$)-alkyl, —S—($C_3$-$C_{12}$)-cycloalkyl, —COO—($C_1$-$C_{12}$)-alkyl, —COO—($C_1$-$C_{12}$)-cycloalkyl, —CONH—($C_1$-$C_{12}$)-alkyl, —CONH—($C_3$-$C_{12}$)-cycloalkyl, —N—[($C_1$-$C_{12}$)-alkyl]$_2$, —OH, —NH$_2$, halogen.

Preferred substituents in this case are —($C_1$-$C_{12}$)-alkyl, —($C_2$-$C_{12}$)-alkenyl, —($C_3$-$C_{12}$)-cycloalkyl, —($C_6$-$C_{20}$)-aryl.

$R^2$ is preferably selected from methyl, ethyl, n-propyl, isopropyl, n-butyl, isobutyl, sec-butyl, tert-butyl, allyl, methylallyl. $R^2$ is particularly preferably allyl or methallyl.

In a preferred embodiment, $R^2$ is selected so that it does not result in formation of mixed carboxylic esters, even in the case of rearrangement of an alkoxy group of the aluminium alkoxide. For this purpose, the aluminium alkoxide used is preferably a compound of the general formula (III):

$$Al(OCH_2R^3)_3 \quad\quad (III),$$

where each of the $R^3$ radicals corresponds to the $R^1$ radical of the respective aldehyde according to formula (I) used.

If the aldehyde is acrolein, the aluminium alkoxide used is therefore preferably a compound of the general formula (III) in which $R^3$ is a vinyl group. If the aldehyde is methacrolein, the aluminium alkoxide used is preferably a compound of the general formula (III) in which $R^3$ is a 2-allyl group.

The support material is characterized in that it is insoluble in the reaction medium and is present as a solid. The support material may be present in this case for example as a powder, moulded body, monolith or mesh.

In one embodiment, the support material is present in the form of particles having a numerical average particle size of 0.2 to 10 mm, preferably 0.5 to 5 mm. In an alternative embodiment, the support material is present as a powder having a numerical average particle size of the powder particles of 10 to 200 μm, preferably 20 to 120 μm. The numerical average particle size of the support material may be determined according to ISO 13320:2009 by laser diffraction particle size analysis. The resulting measured particle size distribution is used to define the mean $d_{50}$, which reflects the particle size not exceeded by 50% of all particles, as the numerical average particle size.

The support material used is preferably an oxidic support. The support material comprises silicon dioxide for example and optionally at least one further metal oxide besides silicon dioxide. The term silicon dioxide is used here as a collective term for the oxides of silicon having the empirical formula $SiO_2$. Silicon dioxide is regarded as a metal oxide within the context of this invention. Suitable further metal oxides are, for example, oxides of aluminium, alkali metals, alkaline earth metals, rare earth metals, Ti, Zr, Cu, Mn, Pb, Sn and Bi.

Silicon dioxide or a material comprising silicon dioxide has proven to be a particularly suitable support material. In this case, the support material preferably should be composed predominantly of silicon dioxide and may optionally comprise aluminium oxide ($Al_2O_3$) and further metal oxides. Suitable further metal oxides in this context are especially oxides of alkali metals, alkaline earth metals, rare earth metals, Ti, Zr, Cu, Mn, Pb, Sn and Bi. The amount of other metal oxides besides silicon dioxide and aluminium oxide is preferably kept low.

In one embodiment, the support material comprises
a) 40-100 mol % silicon,
b) 0-40 mol % aluminium, and
c) 0-20 mol % of at least one further element selected from alkali metals, alkaline earth metals, rare earth metals, Ti, Zr, Cu, Mn, Pb. Sn and Bi;
wherein the molar amount proportions stated refer to the total molar amount of components a) to c), without taking into account the oxygen optionally present in the support material. This statement of the composition without taking oxygen into account is appropriate since some of the elements specified have distinctly different oxidation states and, for example, mixed oxides may also be present. The support material preferably comprises 90-100 mol % silicon, 0-10 mol % aluminium and 0-3 mol % of at least one of the further elements mentioned under c). The support material particularly preferably comprises 95-100 mol % silicon, 0-5 mol % aluminium and none of the further elements mentioned under c). The support material preferably consists of components a) to c) and oxygen.

The support material preferably comprises 89-100% by weight silicon dioxide, particularly preferably at least 92-100% by weight silicon dioxide, most preferably at least 97-100% by weight silicon dioxide, based on the total weight of the support material.

The proportion of further metal oxides other than silicon dioxide, especially of oxides of aluminium, alkali metals, alkaline earth metals, rare earth metals, Ti, Zr, Cu, Mn, Pb, Sn and Bi, is preferably kept low. In one embodiment, the support material therefore comprises 0-11% by weight, preferably 0-8% by weight, particularly preferably 0-3% by weight of oxides of aluminium, alkali metals, alkaline earth metals, rare earth metals, Ti, Zr, Cu, Mn, Pb, Sn and Bi, based on the total weight of the support material.

In one embodiment, the support material comprises 89-100% by weight silicon dioxide, 0-10% by weight aluminium oxide and 0-3% by weight of oxides of alkali metals, alkaline earth metals, rare earth metals, Ti, Zr, Cu, Mn, Pb. Sn and Bi, preferably 92-100% by weight silicon dioxide, 0-8% by weight aluminium oxide and 0-1% by weight of oxides of alkali metals, alkaline earth metals, rare earth metals, Ti, Zr, Cu, Mn, Pb, Sn and Bi, particularly preferably 97-100% by weight silicon dioxide, 0-3% by weight aluminium oxide and 0-0.5% by weight of oxides of alkali metals, alkaline earth metals, rare earth metals, Ti, Zr, Cu, Mn, Pb, Sn and Bi, based on the total weight of the support material.

In one embodiment, the support material comprises 90-100% by weight silicon dioxide and 0-10% by weight aluminium oxide, preferably 95-100% by weight silicon dioxide and 0-5% by weight aluminium oxide, particularly preferably 99-100% by weight silicon dioxide and 0-1% by weight aluminium oxide, based on the total weight of the support material. In this context, the support material particularly preferably consists of the specified proportions of silicon dioxide and optionally aluminium oxide.

In a particularly preferred embodiment the support material is silicon dioxide. This material optionally comprises unavoidable traces of further metal oxides other than silicon dioxide.

The amount of supported aluminium alkoxide is preferably selected such that the molar amount of aluminium, based on the molar amount of aldehyde used, is 0.1 to 10 mol %, preferably 0.5 to 5 mol %, particularly preferably 1 to 3 mol %.

The aldehyde may be reacted in the presence of the supported aluminium alkoxide with or without addition of a solvent. Preferably, no solvent is used.

If a solvent is used, suitable for this purpose are, for example, hydrocarbons such as n-pentane, n-hexane, cyclohexane, heptane, octane, decane etc., aromatic compounds such as benzene, toluene, xylene etc., esters such as ethyl acetate, ethers such as diethyl ether, methyl tert-butyl ether etc.

The aldehyde can be reacted in the presence of the supported aluminium alkoxide, for example at a reaction temperature between 5 and 100° C. The reaction temperature is preferably 10 to 60° C., particularly preferably 15 to 30° C.

The conversion of the aldehyde to the carboxylic ester in the presence of the supported aluminium alkoxide may be carried out continuously or discontinuously (batchwise), a continuous process regime being preferred.

In a continuous process, the average residence time of the reaction mixture in the reactor is preferably 1 minute to 10 hours, particularly preferably 10 minutes to 5 hours. The reactor used in this case may be a fixed bed reactor or another generally known reactor type for these purposes.

The reaction time of the discontinuous method is guided by the time within which the reaction of the aldehyde to the carboxylic ester reaches equilibrium. In the case of a discontinuous process, the reaction time is preferably 0.5 to 72 hours, particularly preferably 1 to 30 hours.

In one embodiment, the method according to the invention comprises a filtration step for removing the supported aluminium alkoxide.

The invention also relates to a method for preparing supported aluminium alkoxides by reacting an aluminium alkoxide with a support material such that the aluminium alkoxide is adsorbed onto the support material.

The aluminium alkoxide and support material used in this case are the aluminium alkoxide described above and the support material described above.

The aluminium alkoxide is reacted with the support material, preferably at a temperature of 10° C. to 80° C., preferably 30° C. to 70° C., particularly preferably 50° C. to 70° C.

In one embodiment, the aluminium alkoxide is reacted with the support material by bringing a solution of the aluminium alkoxide in a solvent into contact with the support material such that the aluminium alkoxide is adsorbed onto the support material.

Useful solvents in which the aluminium alkoxide is initially charged are in this case all solvents in which the aluminium alkoxide has sufficient solubility. It is possible to use, for example, aliphatic or cycloaliphatic hydrocarbons such as n-pentane, n-hexane, cyclohexane, heptane, octane, decane etc., aromatic compounds such as benzene, toluene, xylene etc., esters such as ethyl acetate, ethers such as diethyl ether, methyl tert-butyl ether etc.

The support material is treated with the aluminium alkoxide solution, preferably at a temperature of 10 to 80° C., preferably 30 to 70° C., particularly preferably 50 to 70° C. The duration of treatment is, for example, 1 to 12 hours, preferably 2 to 8 hours, particularly preferably 3 to 5 hours.

The amount of aluminium alkoxide in the solution is, for example, 0.1 to 1 g/ml, preferably 0.2 to 0.5 g/ml, based on the volume of the solution without taking the support material into account.

In one embodiment, the amount of aluminium alkoxide in the solution is 10 to 60% by weight, preferably 20 to 50% by weight, particularly preferably 30 to 40% by weight, based on the total weight of the solution without taking the support material into account.

Following this treatment, the solvent is preferably removed by distillation in order to isolate the supported aluminium alkoxide.

In an alternative embodiment, aluminium alkoxide in solid form is mixed with the support material and optionally heat-treated. By way of example, the heat treatment can be conducted in this case at a temperature of 30 to 70° C., preferably 50 to 70° C.

In a further embodiment, aluminium alkoxide in liquid form is brought into contact with the support material such that the aluminium alkoxide is adsorbed onto the support material. In this case, the aluminium alkoxide is preferably sprayed onto the support material.

In this context, the temperature can be, for example, 10 to 80° C., preferably 30 to 70° C., particularly preferably 50 to 70° C.

In one embodiment, the support material is present in the form of particles having a numerical average particle size of 0.5 to 5 mm. In an alternative embodiment, the support material is present as a powder having a numerical average particle size of the powder particles of 10 to 200 µm, preferably 20 to 120 µm. In these embodiments, the ratio by weight of aluminium alkoxide to support material is preferably 1-60% by weight, preferably 5-50% by weight, particularly preferably 15-45% by weight.

EXAMPLES

Example 1 (Comparative Example Using Homogeneous Catalyst)

1.5 g of Al(OMethallyl)$_3$ (2 mol % Al based on methacrolein) was mixed with 20 g of methacrolein at 20° C. The reaction mixture was stirred at 20° C. for 48 h. Reactant and product were then separated from the catalyst by distillation under reduced pressure and the distillates were analyzed by GC.

Example 2 (Catalyst on SiO$_2$ Support)

Al(OMethallyl)$_3$ (6 g) was dissolved in anhydrous cyclohexane (20 mL) and mixed with 15 g of SiO$_2$ support (Cariact Q10, 1.18-2.36 mm from Fuji Silysia Chemical). This mixture was temperature-controlled at 60° C. for 4 h and then cooled. The solvent was removed under reduced pressure to obtain a catalyst (1).

5.25 g of this supported catalyst (1) (2 mol % Al based on methacrolein) was mixed with 20 g of methacrolein at 20° C. The reaction mixture was stirred at 20° C. for 48 h. The product mixture was then separated by filtration and analyzed by GC.

Example 3 (Catalyst on SiO$_2$—Al$_2$O$_3$ Support)

Al(OMethallyl)$_3$ (6 g) was dissolved in anhydrous cyclohexane (20 mL) and mixed with 15 g of SiO$_2$—Al$_2$O$_3$ support (65 μm powder, 7 wt % Al$_2$O$_3$). This mixture was temperature-controlled at 60° C. for 4 h and then cooled. The solvent was removed under reduced pressure to obtain a catalyst (2).

5.25 g of this supported catalyst (2) (2 mol % Al based on methacrolein) was mixed with 20 g of methacrolein at 20° C. The reaction mixture was stirred at 20° C. for 48 h. The product mixture was then separated by filtration and analyzed by GC.

Example 4 (Catalyst on SiO$_2$—Al$_2$O$_3$—MgO Support)

Al(OMethallyl)$_3$ (6 g) was dissolved in anhydrous cyclohexane (20 mL) and mixed with 15 g of SiO$_2$—Al$_2$O$_3$—MgO support (20-100 μm powder, 6.2 wt % Al$_2$O$_3$, 4 wt % MgO). This mixture was temperature-controlled at 60° C. for 4 h and then cooled. The solvent was removed under reduced pressure to obtain a catalyst (3).

5.25 g of this supported catalyst (3) (2 mol % Al based on methacrolein) was mixed with 20 g of methacrolein at 20° C. The reaction mixture was stirred at 20° C. for 48 h. The product mixture was then separated by filtration and analyzed by GC.

The product parameters determined in Examples 1-4 are compiled in the following table.

| No. | Support | Methacrolein Conversion (%) | Methallyl methacrylate Yield (%) | Methallyl methacrylate Selectivity (%) |
|---|---|---|---|---|
| 1 | None | 58.6 | 51.8 | 88.4 |
| 2 | SiO$_2$ | 80.2 | 79.6 | 99.3 |
| 3 | SiO$_2$—Al$_2$O$_3$ | 41.1 | 21.7 | 52.8 |
| 4 | SiO$_2$—Al$_2$O$_3$—MgO | 12.3 | 2.8 | 22.8 |

These examples show that supported aluminium alkoxides are effective catalysts for the conversion of aldehydes to carboxylic esters. It is particularly shown here that the efficacy of the catalysts can be increased by selection of a suitable support material. A support material based on silicon dioxide having a low proportion of aluminium oxide and other metal oxides leads to a higher yield. The best results are achieved using pure silicon dioxide as support.

Example 5 (Recycling the Catalyst)

5.25 g of supported catalyst (1) was mixed with 20 g of methacrolein (<100 ppm water) at 20° C. The reaction mixture was stirred at 20° C. for 48 h. The product mixture was then separated by filtration and analyzed by GC (catalyst use 1). Fresh methacrolein (20 g) was added and the reaction mixture was stirred at RT for a further 48 h and analyzed by GC after filtration (catalyst use 2). Thereafter, the catalyst was again mixed with 20 g of fresh methacrolein and stirred at 30° C. for 48 h. The results of these experiments are compiled in the following table:

| No. (catalyst use) | Methacrolein Conversion (%) | Methallyl methacrylate Yield (%) | Methallyl methacrylate Selectivity (%) |
|---|---|---|---|
| 1 | 80.2 | 79.6 | 99.3 |
| 2 | 78.0 | 76.5 | 98.1 |
| 3 | 77.6 | 76.0 | 98.0 |

This example shows that the method according to the invention also allows reuse of the supported aluminium alkoxide.

The invention claimed is:
1. A method for preparing a carboxylic ester, the method comprising:
reacting (meth)acrolein in the presence of an aluminum alkoxide applied to a support material comprising silicon dioxide.
2. The method according to claim 1, wherein the aluminum alkoxide is a compound of formula (II):

$$Al(OR^2)_3 \quad (II),$$

wherein each $R^2$ radical is independently of one another a —(C$_1$-C$_{12}$)-alkyl group or a —(C$_2$-C$_{12}$)-alkenyl group and each $R^2$ radical may independently of one another optionally be substituted by one or more substituents selected from the group consisting of —(C$_1$-C$_{12}$)-alkyl, —(C$_3$-C$_{12}$)-cycloalkyl, —(C$_4$-C$_{12}$)-heterocycloalkyl, —(C$_6$-C$_{20}$)-aryl, —(C$_4$-C$_{20}$)-heteroaryl, —O—(C$_1$-C$_{12}$)-alkyl, —O—(C$_3$-C$_{12}$)-cycloalkyl, —S—(C$_1$-C$_{12}$)-alkyl, —S—(C$_3$-C$_{12}$)-cycloalkyl, —COO—(C$_1$-C$_{12}$)-alkyl, —COO—(C$_3$-C$_{12}$)-cycloalkyl, —CONH—(C$_1$-C$_{12}$)-alkyl, —CONH—(C$_3$-C$_{12}$)-cycloalkyl, —N—[(C$_1$-C$_{12}$)-alkyl]$_2$, —OH, —NH$_2$, and a halogen atom.

3. The method according to claim 1, wherein the aluminum alkoxide is a compound of formula (III)

Al(OCH$_2$R$^3$)$_3$ (III), wherein each of the R$^3$ radicals corresponds to C$_2$ alkenyl or methyl substituted C$_2$ alkenyl.

4. The method according to claim 2, wherein each R$^2$ group is, independently, a group selected from the group consisting of methyl, ethyl, n-propyl, isopropyl, n-butyl, isobutyl, sec-butyl, tert-butyl, allyl, and 2-methylallyl.

5. The method according to claim 1, wherein said reacting is carried out at a reaction temperature of 10 to 60° C.

6. The method according to claim 1, wherein said reacting is carried out continuously.

7. The method according to claim 1, wherein said (meth) acrolein is reacted without addition of solvent.

* * * * *